US011912981B2

(12) United States Patent
Choi et al.

(10) Patent No.: US 11,912,981 B2
(45) Date of Patent: Feb. 27, 2024

(54) STREPTOMYCES SP. SNC087 STRAIN ISOLATED FROM SEAWATER, METHOD FOR PRODUCING STAUROSPORINE USING SAME, METHOD OF CULTURING SAME, AND PURE CULTURE MEDIUM OF SAME

(71) Applicant: National Marine Biodiversity Institute of Korea, Seocheon-gun (KR)

(72) Inventors: Grace Choi, Gunsan-si (KR); Jeong Min Lee, Gunsan-si (KR); Mi Jin Yim, Gunsan-si (KR); Sang Jip Nam, Gwangmyeong-si (KR)

(*) Notice: Subject to any disclaimer, the term of this patent is extended or adjusted under 35 U.S.C. 154(b) by 338 days.

(21) Appl. No.: 17/280,891

(22) PCT Filed: Jun. 18, 2020

(86) PCT No.: PCT/KR2020/007906
§ 371 (c)(1),
(2) Date: Mar. 28, 2021

(87) PCT Pub. No.: WO2020/256434
PCT Pub. Date: Dec. 24, 2020

(65) Prior Publication Data
US 2022/0002666 A1 Jan. 6, 2022

(30) Foreign Application Priority Data
Jun. 19, 2019 (KR) .......................... 10-2019-0072620

(51) Int. Cl.
*C12N 1/20* (2006.01)
*C12P 17/18* (2006.01)
*C12R 1/465* (2006.01)

(52) U.S. Cl.
CPC ............ *C12N 1/205* (2021.05); *C12P 17/188* (2013.01); *C12R 2001/465* (2021.05)

(58) Field of Classification Search
CPC ......... C12N 1/205; C12N 1/20; C12P 17/188; C12P 17/08; C12R 2001/465
See application file for complete search history.

(56) References Cited

FOREIGN PATENT DOCUMENTS

| KR | 10-2010-0069073 A | 6/2010 |
| KR | 10-1938738 B1 | 4/2019 |

OTHER PUBLICATIONS

Dharmaraj, Selvakumar. "Marine Streptomyces as a novel source of bioactive substances." World Journal of Microbiology and Biotechnology 26 (2010): 2123-2139. (Year: 2010).*
Sui, Jin-Lei, et al. "*Streptomyces sanyensis* sp. nov., isolated from mangrove sediment." International journal of systematic and evolutionary microbiology 61.7 (2011): 1632-1637. (Year: 2011).*
Stackebrandt, Erko, et al. "Deposit of microbial strains in public service collections as part of the publication process to underpin good practice in science." SpringerPlus 3 (2014): 1-4. (Year: 2014).*
International Search Report for PCT/KR2020/007906 dated Oct. 8, 2020.

* cited by examiner

*Primary Examiner* — Lora E Barnhart Driscoll
*Assistant Examiner* — Candice Lee Swift

(57) ABSTRACT

The present invention provides a *Streptomyces* sp. SNC087 strain (KCCM12505P) that is isolated from seawater and produces staurosporine, a method for producing staurosporine using the same, a method for culturing the same, and a pure culture medium of the same.

1 Claim, 7 Drawing Sheets

Specification includes a Sequence Listing.

[FIG. 1]
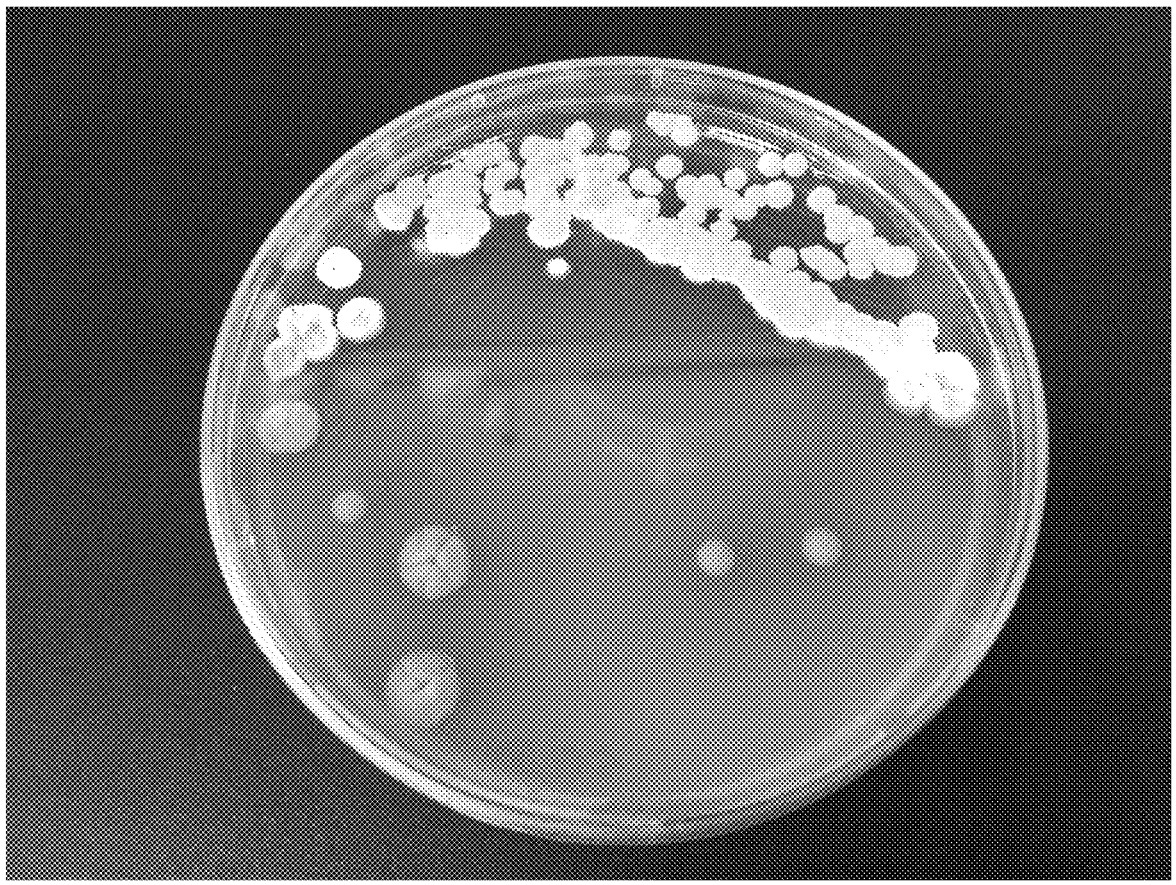

[FIG. 2]
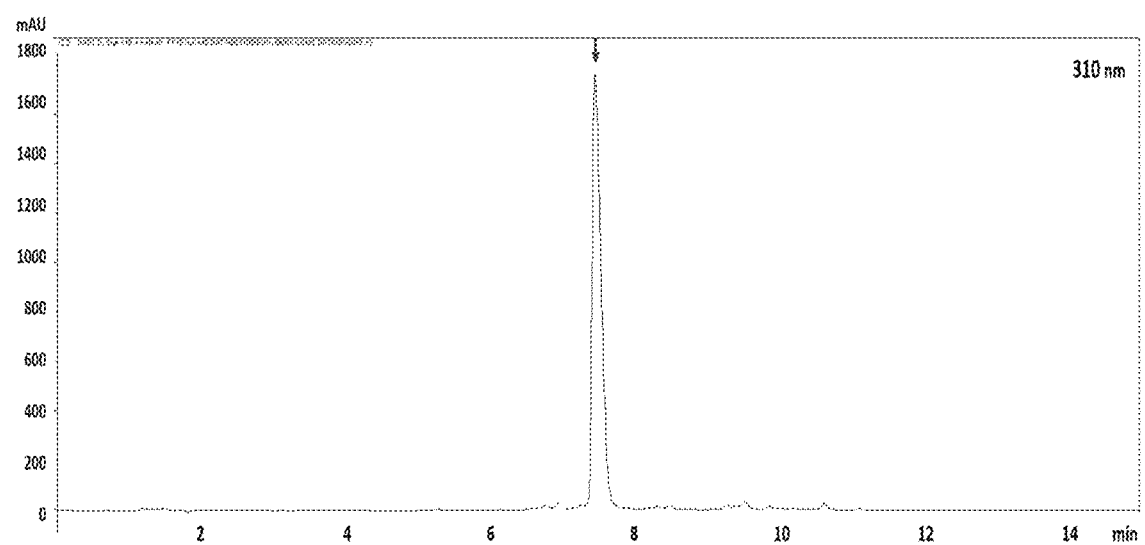

[FIG. 3]
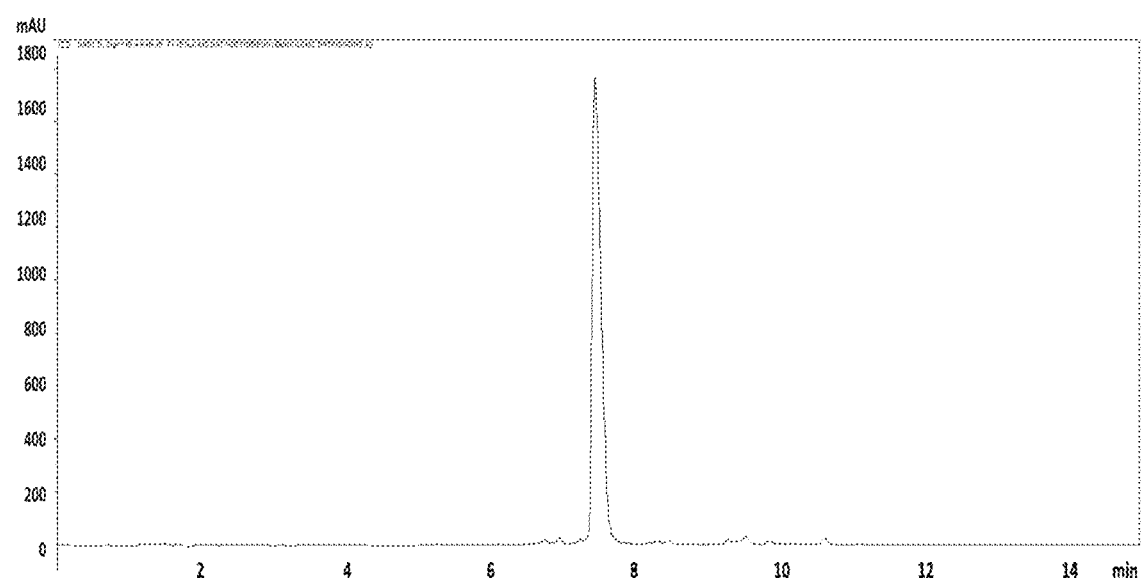

[FIG. 4]
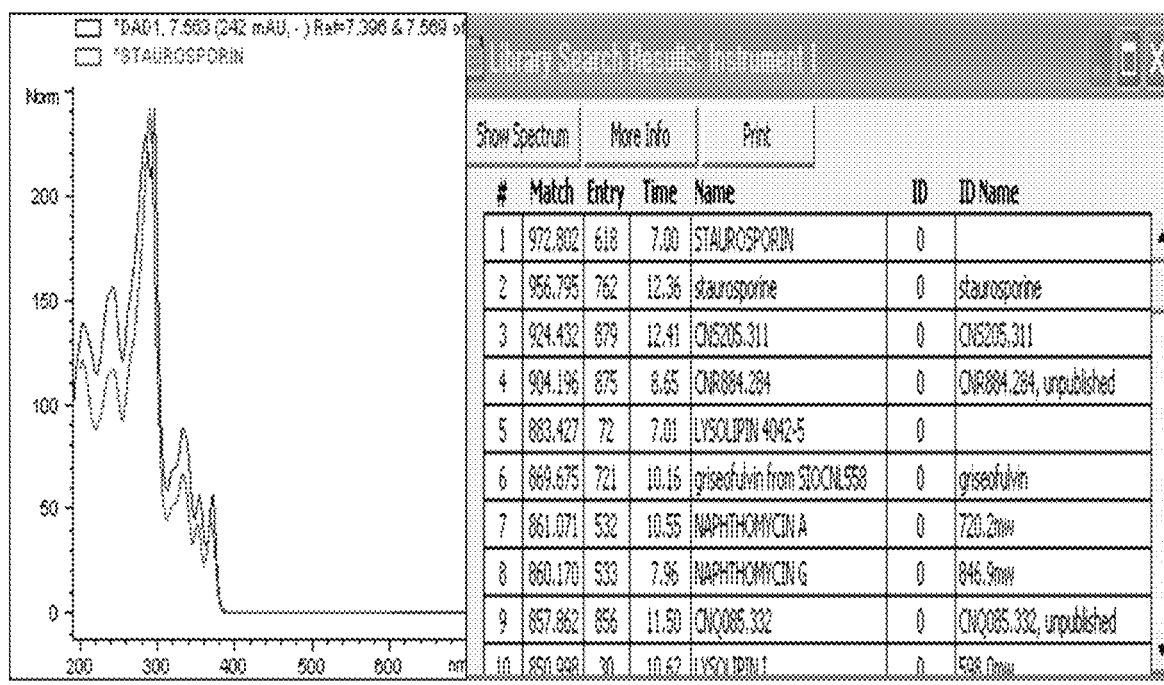

[FIG. 5]
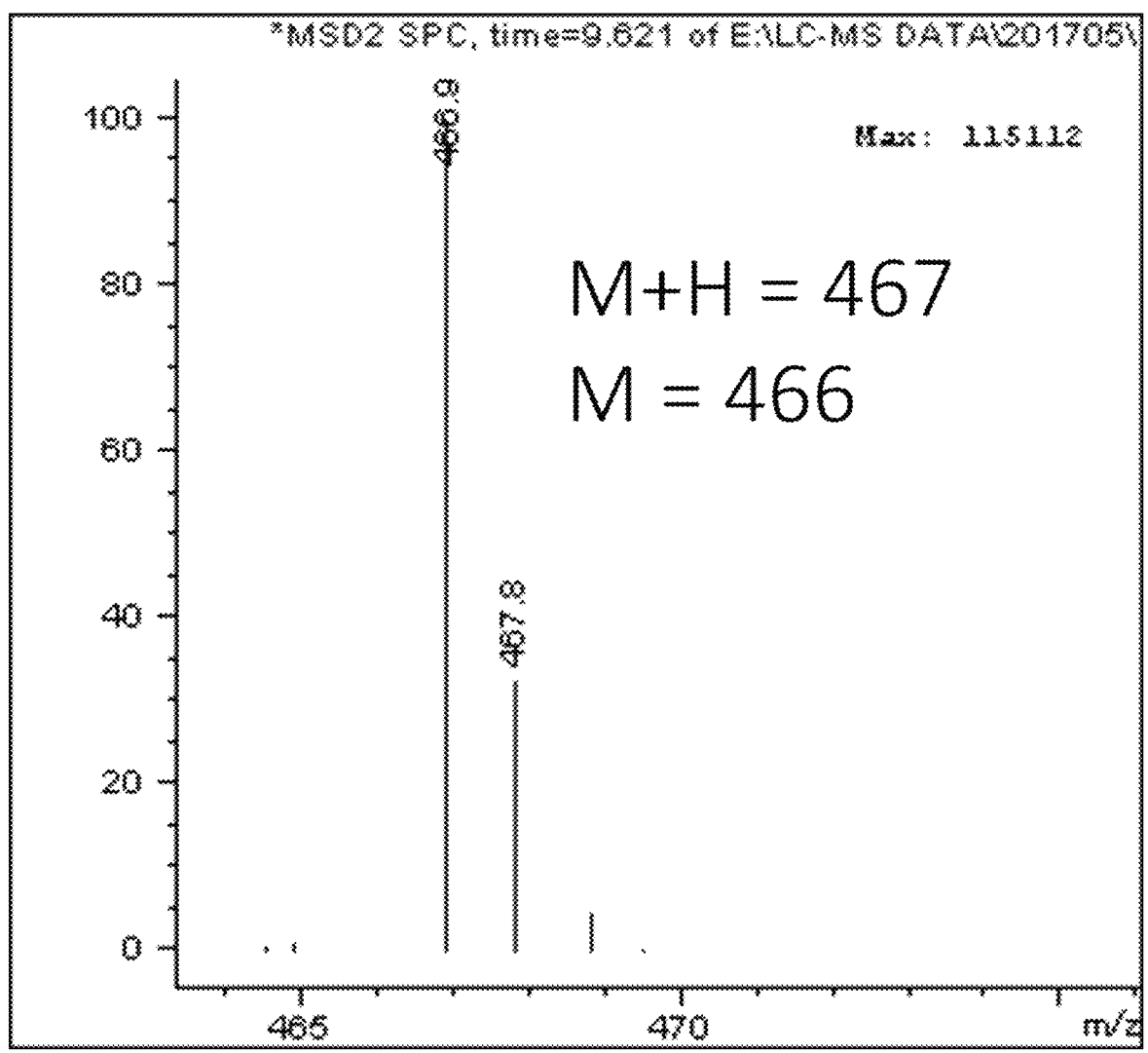

[FIG. 6]
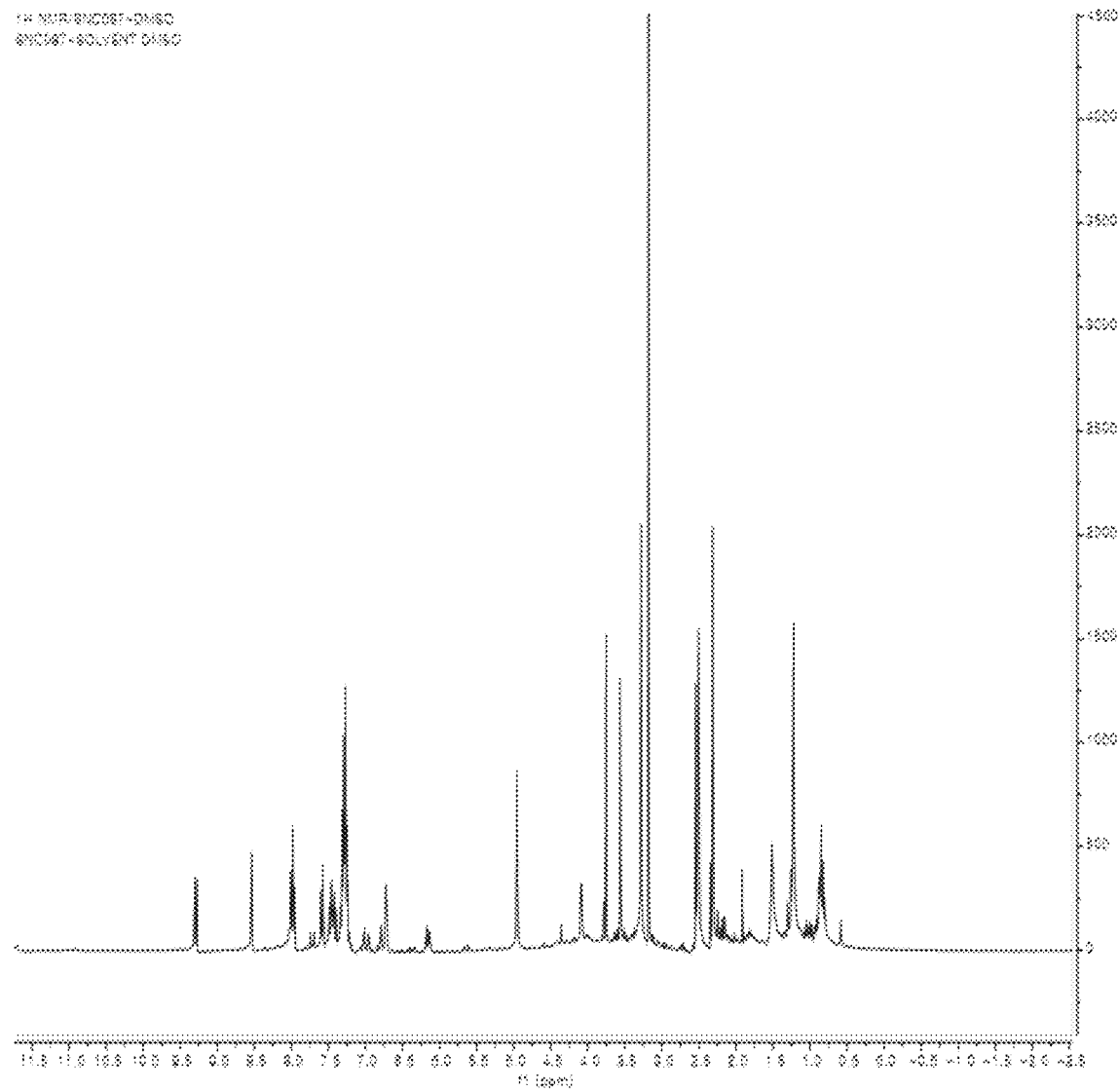

[FIG. 7]
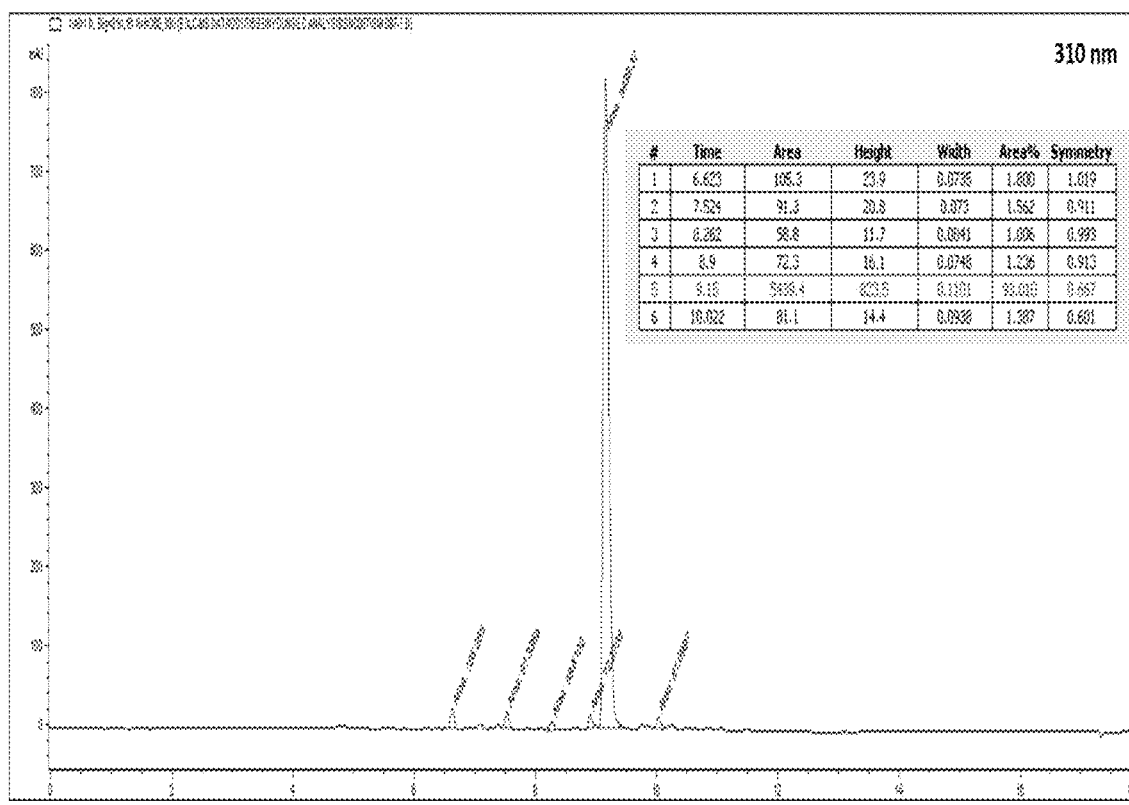

SEQUENCE LISTING

```
<160> NUMBER OF SEQ ID NOS: 1

<210> SEQ ID NO 1
<211> LENGTH: 1397
<212> TYPE: DNA
<213> ORGANISM: Streptomyces sp.
<220> FEATURE:
<221> NAME/KEY: rRNA
<222> LOCATION: (1)..(1397)
```

```
<400> SEQUENCE: 1
tgcagtcgac gatgaacctc cttcgggagg ggattagtgg cgaacgggtg agtaacacgt    60
gggcaatctg ccctgcactc tgggacaagc cctggaaacg gggtctaata ccggatacga   120
ctcgggaggg catccttccg ggtggaaagc tccggcggtg caggatgagc ccgcggccta   180
tcagcttgtt ggtggggtga tggcctacca aggcgacgac gggtagccgg cctgagaggg   240
cgaccggcca cactgggact gagacacggc ccagactcct acgggaggca gcagtgggga   300
atattgcaca atgggcgaaa gcctgatgca gcgacgccgc gtgagggatg acggccttcg   360
ggttgtaaac ctctttcagc agggaagaag cgcaagtgac ggtacctgca gaagaagcgc   420
cggctaacta cgtgccagca gccgcggtaa tacgtagggc gcaagcgttg tccgaatta    480 ttgggcgtaa agagctcgta ggcggcttgt cgcgtcggat gtgaaagctc ggggcttaac   540
cccgggtctg cattcgatac gggcaggcta gagtgtggta ggggagatcg gaattcctgg   600
tgtagcggtg aaatgcgcag atatcaggag gaacaccggt ggcgaaggcg gatctctggg   660
ccattactga cgctgaggag cgaaagcgtg gggagcgaac aggattagat accctggtag   720
tccacgccgt aaacgttggg aactaggtgt tggcgacatt ccacgtcgtc ggtgccgcag   780
ctaacgcatt aagttccccg cctggggagt acggccgcaa ggctaaaact caaaggaatt   840
gacgggggcc cgcacaagca gcggagcatg tggcttaatt cgacgcaacg cgaagaacct   900
taccaaggct tgacatatac cggaaagtgc tagagatagt gccccccttg tggtcggtat   960
acaggtggtg catggctgtc gtcagctcgt gtcgtgagat gttgggttaa gtcccgcaac  1020
gagcgcaacc cttgttctgt gttgccagca tgcccttcgg ggtgatgggg actcacagga  1080
gactgccggg gtcaactcgg aggaaggtgg ggacgacgtc aagtcatcat gccccttatg  1140
tcttgggctg cacacgtgct acaatggccg gtacaatgag ctgcgatgcc gtgaggcgga  1200
gcgaatctca aaaagccggt ctcagttcgg attggggtct gcaactcgac cccatgaagt  1260
cggagttgct agtaatcgca gatcagcatt gctgcggtga atacgttccc gggccttgta  1320
cacaccgccc gtcacgtcac gaaagtcggt aacacccgaa gccggtggcc caacccttg   1380 tgggagggag cttcgaa                                                1397
```

STREPTOMYCES SP. SNC087 STRAIN ISOLATED FROM SEAWATER, METHOD FOR PRODUCING STAUROSPORINE USING SAME, METHOD OF CULTURING SAME, AND PURE CULTURE MEDIUM OF SAME

TECHNICAL FIELD

The present invention relates to a strain of SNC087 in the genus *Streptomyces* ("*Streptomyces* sp. SNC087 strain") isolated from seawater, a method for producing staurosporine using the strain, a method for culturing the strain, and a pure culture solution of the strain. More particularly, the present invention relates to a *Streptomyces* sp. SNC087 strain isolated from seawater, which has excellent production capacity of staurosporine with anticancer activity and enables stable mass production thereof, thereby contributing to expansion of foods, pharmaceuticals and other related industries and public health, as well as a method for culturing the strain and a pure culture solution of the strain.

Background Art

Staurosporine was first isolated from *Streptomyces staurosporeus* in 1977. Staurosporine is known to have antibacterial and antihypertensive activities. The main biological activity of staurosporine is an ability to inhibit protein kinase C by preventing ATP from binding to kinase. This is caused by strong affinity of staurosporine with ATP binding sites. In addition, staurosporine induces apoptosis by activated caspase-3 to stop cell division in G1 or G2 stage of the cell cycle. Therefore, in clinical studies, it was observed that staurosporine encapsulated with liposome nanoparticles has anticancer effects without side effects in an experiment performed on mice as a target.

Due to anticancer effects and various biological activities of staurosporine, various studies are being conducted, including success in total synthesis of not only staurosporine but also analog substances.

With regard to staurosporine, domestic and foreign patent documents disclose various uses such as a study on a primer set for detecting staurosporine-producing actinomycetes and a detection method using the same (Korean Patent No. 1017885490000), a use of staurosporine derivatives for treatment of ocular angiogenic diseases (Korean Patent No. 1006984490000), a pharmaceutical use of staurosporine derivatives (U.S. Pat. No. 8,575,146), a pharmaceutical substance containing staurosporine (U.S. Pat. No. 5,736,542), a staurosporine culture process (European Patent Application No. 91102374.5), a purification process of staurosporine (European Patent No. 02272850), an apoptosis inducing agent having novel inhibitory effects against intracellular parasitic microorganisms (Japanese Patent Application No. 17125020), a protein kinase inhibitor for treating neurological diseases (Japanese Patent Application No. 17357071), etc.

Currently, staurosporine is being sold by reagent vendors at a high price of 2 million won or more per 1 mg. Accordingly, a stable mass production method of staurosporine, which has proven various uses thereof, and a new proposal for stabilization of the price are required.

DISCLOSURE

Technical Problem

The present invention has been proposed to overcome the problems of the prior art as described above, and an object thereof is to provide a novel *Streptomyces* sp. SNC087 strain isolated from seawater, which has excellent production capacity of staurosporine with anticancer activity and enables stable mass production thereof, thereby contributing to expansion of foods, pharmaceuticals and other related industries and public health, as well as a method for culturing the strain and a pure culture solution of the strain.

Technical Solution

The above-described technical objects of the present invention can be accomplished by the following means.
(1) A *Streptomyces* sp. SNC087 strain (KCCM12505P) producing staurosporine, which is isolated from seawater.
(2) A method for producing staurosporine from a culture product by incubating a *Streptomyces* sp. SNC087 strain (KCCM12505P).
(3) A method for culturing a *Streptomyces* sp. SNC087 strain (KCCM12505P), characterized in that, after primary culture of the *Streptomyces* sp. SNC087 strain (KCCM12505P) in a solid medium, the resulting colonies are inoculated in a liquid medium to culture the same.
(4) The method for culturing a *Streptomyces* sp. SNC087 strain (KCCM12505P) according to above (3), wherein the liquid medium is a SYP liquid medium.
(5) The method for culturing a *Streptomyces* sp. SNC087 strain (KCCM12505P) according to above (3), wherein the SYP liquid medium is used to incubate the colonies at 25 to 29° C. and 100 to 200 rpm while shaking the same.
(6) A pure culture solution of a *Streptomyces* sp. SNC087 strain (KCCM12505P).

Advantageous Effects

As described above, according to the present invention, excellent production capacity of staurosporine having anticancer activity is achieved and stable mass-production may be possible, thereby contributing to expansion of foods, pharmaceuticals and other related industries, as well as public health.

DESCRIPTION OF DRAWINGS

FIG. 1 is a photograph showing the morphology of *Streptomyces* sp. SNC087 strain isolated from seawater in a SYP solid medium.

FIG. 2 illustrates a reverse-phase liquid chromatography (UV 310 nm) of the entire extract of the cultured SNC087 strain, wherein a red arrow indicates staurosporine.

FIG. 3 is liquid chromatography-based chromatogram data measured for the extract of the SNC087 strain obtained in the present invention.

FIG. 4 illustrates comparison results of UV spectrum of a large peak (staurosporine) at 7.6 minutes in the liquid chromatography-based chromatogram of the SNC087 extract obtained in the present invention with In-house database.

FIG. 5 illustrates mass spectrum data of the large peak at 7.6 minutes in the liquid chromatography-based chromatogram of the SNC087 extract obtained in the present invention.

FIG. 6 illustrates NMR data of the SNC087 extract obtained in the present invention.

FIG. 7 illustrates reverse-phase column liquid chromatography results to confirm a content of staurosporine in the crude extract of the SNC087 strain obtained in the present invention and results of calculating the content of staurosporine contained in the extract using the area calculation method.

PREFERRED EMBODIMENTS OF INVENTION

The present inventors prepared an extract using ethyl acetate after liquid culture of the *Streptomyces* sp. SNC087 strain isolated from seawater, and isolated a staurosporine compound represented by Formula 1 below to identify a structure of the compound, and then the present invention has been completed by evaluating a production amount of the compound.

[Formula 1]

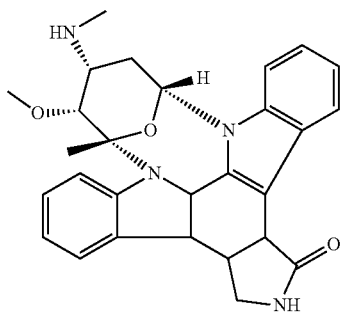

In the present invention, a *Streptomyces* sp. SNC087 strain isolated from seawater may be provided. Hereinafter, a process of obtaining and identifying the *Streptomyces* sp. SNC087 strain (hereinafter, referred to as "SNC087 strain") according to the present invention will be described in detail.

The present inventors collected seawater near Ilgwang Beach in Gijang-gun, Busan, and then added 100 μl of the collected seawater to a Mar4 solid medium (2 g kelp meal, 2 g D-mannitol, 1 g fish meal, 20 g/L KBr, 8 g/L Fe$_2$(SO$_4$)$_3$·4H$_2$O, ml DMSO, 970 ml filtered seawater, 21 g agar) for inoculation, and cultured at 27° C. to produce a single strain, followed by inoculation of the single strain again in a SYP solid medium (10 g starch, 2 g yeast, 4 g peptone, 1 L filtered seawater, 21 g agar), thus to isolate and select pure strains.

The SNC087 strain isolated as described above was observed to have a strain morphology belonging to the typical *Streptomyces* genus (see FIG. 1).

The *Streptomyces* sp. SNC087 strain according to the present invention may have a 16S rRNA gene nucleotide sequence represented by SEQ ID NO: 1 and may secrete staurosporine represented by Formula 1 below as a secondary metabolite. The *Streptomyces* sp. SNC087 strain was deposited with the Korea Microbial Conservation Center on Apr. 30, 2019, and was given the accession number KCCM12505P.

The nucleotide sequence of the 16S rRNA gene of the *Streptomyces* sp. SNC087 strain according to the present invention is as follows (SEQ ID NO: 1):

(SEQUENCE)
AGCGCAACCCTTGTTCTGTGTTGCCAGCATGCCCTTCGGGGTGATGGGGAC

TCACAGGAGACTGCCGGGGTCAACTCGGAGGAAGGTGGGGACGACGTCAAG

TCATCATGCCCCTTATGTCTTGGGCTGCACACGTGCTACAATGGCCGGTAC

-continued

AATGAGCTGCGATGCCGTGAGGCGGAGCGAATCTCAAAAAGCCGGTCTCAG

TTCGGATTGGGGTCTGCAACTCGACCCCATGAAGTCGGAGTTGCTAGTAAT

CGCAGATCAGCATTGCTGCGGTGAATACGTTCCCGGGCCTTGTACACACCG

CCCGTCACGTCACGAAAGTCGGTAACACCCGAAGCCGGTGGCCCAACCCCT

TGTGGGAGGGAGCTTCGAA

The 16S rRNA gene sequence of the *Streptomyces* sp. SNC087 strain showed 99.9% homology with the 16S rRNA gene sequence of *Streptomyces sanyensis* 219820 strain registered in NCBI GenBank. However, it was confirmed in the examples of the present invention that the strain of the present invention has a production ability of 4 times or more superior to a production amount of staurosporine produced by the strain *Streptomyces sanyensis* 219820 under the same conditions. Therefore, it is considered that, even with a small difference in genes in an aspect of position of genes, this difference may possibly induce a mutation at the activation site of the gene related to production of staurosporine, and thus may affect the production ability of staurosporine.

Hereinafter, the present invention will be described in more detail with reference to examples, but these examples are merely for facilitating understanding of the subject matters of the present invention and should not be construed as limiting the scope of the present invention.

[Example 1] Strain Detection and Selection from Seawater

In 2014, seawater was collected at Ilgwang Beach in Gijang-gun, Busan. 100 μl of the collected seawater was added to a Mar4 solid medium (2 g kelp meal, 2 g D-mannitol, 1 g fish meal, 20 g/L KBr, 8 g/L Fe$_2$(SO$_4$)$_3$·4H$_2$O, 30 ml DMSO, 970 ml filtered seawater, 21 g agar) for inoculation, and cultured at 27° C. to produce a single strain, followed by inoculation of the obtained strain again in a SYP solid medium (10 g starch, 2 g yeast, 4 g peptone, 1 L filtered sea water, 21 g agar), thus to isolate and select pure strains. As shown in FIG. 1, the purely isolated SNC087 strain was observed in the same morphology as the strains belonging to the genus *Streptomyces*. In order to identify the strain, 1 ml of the strain cultured at 27° C. for 5 days in the SYP liquid medium was taken and was subjected to extraction of genomic DNA according to the manufacturer's protocol using "Tissue Genome DNA Isolation Kit" (Cosmogenetech Co., Ltd., Seoul, South Korea). PCR was performed using 27F and 1492R primers for amplification of 16S rRNA gene for species analysis. The PCR product was purified using a "PCR purification kit" (Cosmogenetech Co., Ltd., Seoul, South Korea), and then, was subjected to analysis of nucleotide sequence using a capillary electrophoresis machine (Applied Biosystems 3730XL). The 16S rRNA gene sequence obtained from the resulting SNC087 strain was compared with information of previously reported strains by utilizing BLAST search of the GenBank/EMBL/DDBJ database. As a result, the 16S rRNA gene sequence of the SNC087 strain showed 99.9% homology with that of *Streptomyces sanyensis* 219820 strain, whereby the SNC087 strain was determined as a strain belonging to the genus *Streptomyces*.

[Example 2] Mass Liquid Culture of *Streptomyces* sp. SNC087 Strain

Each 20 L of SNC087 was incubated in 1 L SYP liquid medium in 2.5-L Ultra Yield Flask at 27° C. and 150 rpm for 7 days while shaking the same, and then 20 L of ethyl acetate was added thereto. After one day, the extracted ethyl acetate layer was obtained. The ethyl acetate layer was dried by a rotary evaporator to obtain 1.5 g of final product.

[Example 3] Confirmation of Production of Staurosporine Compound 1.5 g of crude extract was analyzed by a reverse-phase column chromatography-mass analyzer (LC-MS) using C18 silica, wherein the analyzer includes 1% formic acid in $H_2O$ and 1% formic acid in acetonitrile and involves a stepwise gradient of 5 to 100% acetonitrile (containing 1% formic acid). As a result of comparing chromatography data at UV 310 nm with In-house UV spectrum database and monitoring MS data, homology between a peak of staurosporine at 7.6 minutes and the peak of staurosporine in the database, MS data values corresponding to a molecular weight of 466 and NMR data could be confirmed. The present inventors could obtain about 1.4 g of staurosporine from the crude extract after 20 L liquid culture of the SNC087 strain.

[Example 4] Identification of Compound

Liquid chromatography-based chromatogram data was obtained for the SNC087 extract obtained in Example 3 as shown in FIG. 3, whereby a large peak (staurosporine) at 7.6 minutes was observed at UV wavelength of 310 nm in the chromatogram confirmation.

Further, as a result of comparing the UV spectrum of the large peak (staurosporine) at 7.6 minutes in the liquid chromatography-based chromatogram of the SNC087 extract as shown in FIG. 4 with In-house database, and examining mass spectrum data of the large peak at 7.6 minutes in the liquid chromatography-based chromatogram of the SNC087 extract as shown in FIG. 5 and NMR data of the SNC087 extract (solvent: DMSO-d6) as shown in FIG. 6, staurosporine represented by Formula 1 below was identified.

[Formula 1]

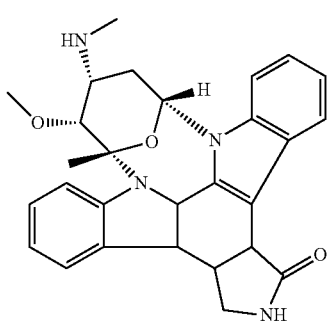

[Example 5] Calculation of Staurosporine Production Amount from SNC087 Strain

In order to determine a content of staurosporine in the crude extract of SNC087 strain, the present inventors injected 60 μg of the crude extract during material purification using reverse-phase column liquid chromatography and calculated the content of staurosporine contained in the extract by an area calculation method. Further, as a result of the calculation shown in FIG. 7, 93% of the injected extract was identified as staurosporine. According to this result, it could be confirmed that 55.8 μg of staurosporine is contained in 60 μg of the crude extract extracted from the culture solution of the SNC087 strain.

In mass culture of 20 L SNC087 strain attempted by the present inventors, 1.5 g of crude extract was obtained, and 1.4 g of staurosporine could be obtained from the crude extract. This amount showed a high productivity of 70 mg/L of culture solution. When compared to *S. sanyensis* 219820, which has 99.9% similarity to the SNC087 strain obtained by the present inventors, it could be confirmed that a production amount in the present invention is 4 times or more superior to that of the prior art, that is, 325.1 mg of staurosporine produced by *S. sanyensis* 219820 in 20 L culture according to the previously reported literature.

Staurosporine is actively used as an anticancer agent in the clinical stage. Further, staurosporine still being studied in many fields has been confirmed to have a yield of 24% after undergoing total synthesis including five stages. With regard to the medium components and culture methods suggested by the present inventors and the obtained SNC087 strain, it could be demonstrated that high yield staurosporine can be obtained by a biological process rather than a chemical method.

As described above, the present invention has been described with reference to preferred embodiments of the present invention, but it will be understood that those skilled in the art can variously modify and change the present invention within a range of the present invention without departing from the spirit and scope of the present invention described in the appended claims.

The invention claimed is:

1. A method for producing staurosporine from a culture product by incubating a *Streptomyces* sp. SNC087 strain (KCCM12505P).

\* \* \* \* \*